United States Patent

Reim

[19]

[11] Patent Number: 5,963,297
[45] Date of Patent: Oct. 5, 1999

[54] ORTHOKERATOLOGY CONTACT LENS AND METHOD THEREFOR

[76] Inventor: Thomas Russell Reim, 3061 Rio Palma N, Indialantic, Fla. 32903

[21] Appl. No.: 08/885,297

[22] Filed: Jun. 27, 1997

[51] Int. Cl.⁶ ..................................................... G02B 7/04
[52] U.S. Cl. .................................. 351/160 R; 351/160 H; 351/161; 351/177
[58] Field of Search ........................... 351/160 R, 160 H, 351/161, 162, 177

[56] References Cited

U.S. PATENT DOCUMENTS

| | | | |
|---|---|---|---|
| 4,952,045 | 8/1990 | Stoyan | 351/160 R |
| 5,191,365 | 3/1993 | Stoyan | 351/160 R |
| 5,349,395 | 9/1994 | Stoyan | 351/160 R |
| 5,428,412 | 6/1995 | Stoyan | 351/160 R |

OTHER PUBLICATIONS

"A Programmed Approach to RGP Control of Myopia," published Jun. 1992 in Review of Optometry, authors: Rodger T. Kame and Jon K. Hayashida.
"Optimal Lens Choices for Orthokeratology," date of publication unknown, author: John Schachet.
"A New Approach to Orthokeratology," published Apr. 1992 in Contact Lens Spectrum, authors: Donald H. Harris and Nick Stoyan.
"Orthokeratology Using The One Piece Bifocal," date of publication unknown, author: Alfred A. Fontana.
"The Successful Ortho–K Patient," published Feb. 1995 in Contacto, author: Alfred A. Fontana.
"Orthokeratology," published Nov. 1975 in Optometrists Exchange, author: Alfred A. Fontana.
"Flatten The Cornea The Nonsurgical Way," published Apr. 15, 1995 in Review Of Optometry, author: Rodger T. Kame.
"Orthokeratology—Night Therapy and Night Reduction," published Nov. 1992 in Spectrum, author: Stuart Grant.
"Orthokeratology," published 1993 in Clinical Contact Lens Pratice, authors: P. Sarita Soni and Douglas G. Horner.
"Corneal Change Accompanying Orthokeratology—Plastic or Elastic? Results of a Randomized Controlled Clinical Trial," published Dec. 1983 in Archives Of Ophtalmology, authors: Keith A. Poise, Richard J. Brand, David W. Vastine, and Joan S. Schwalbe.
"Reconsider Orthokeratology—Could it be optometry's answer to Radical K?," published Jul. 1993 in Spectrum, author: William Hunter.
"Corrective Measures For Myopia," published Jan.–Feb. 1990 in Diagnostic and Surgical Techniques, authors: Douglas R. Wilson and Arthur H. Keeney.
"Symposium on Medical and Surgical Diseases of the Cornea," published 1980 in Transactions of teh New Orleans Academy of Ophtalmology, authors: Jose Barraquer, Perry S. Binder, Jorge N. Buxton, Max Fine, Dan B. Jones, Peter R. Laibson, Anthony B. Nesburn, David Patton, and Richard C. Troutman.
"Orthokeratology Handbook," published 1995 buy Butterworth Heinmann, authors: Todd D. Winkler and Roger T. Kane.
"OK–3™ Fitting Nonogram," published 1993, author: Nick Stoyan.
"OK™ Lens Fitting Guide," revised Feb. 28, 1995, author: Nick Stoyan.
"OK™ Lens Fitting Guide," dated May 1994, author: Nick Stoyan.
"OK™ Lens Design Update," copyright 1989, 1995, author: Nick Stoyan.

*Primary Examiner*—Scott J. Sugarman

[57] ABSTRACT

A contact lens (400) and orthokeratology method for correcting a patient's vision. The contact lens (400) has an optical zone (406) for compressing a central potion of a cornea. The contact lens (400) also includes an alignment zone (410) that has curvature less than a measured curvature of a portion of the cornea under the alignment zone (410). This curvature of the alignment zone (410) creates a large corneal bearing area (402) that provides a centering force to maintain the optical zone (406) substantially at the center of corneal visual axis. While wearing the contact lens (400), forces from the alignment zone (410) and optical zone (406) cooperate to flatten the central portion of the cornea by maintaining compression at the central portion of the cornea, resulting in visual correction.

15 Claims, 2 Drawing Sheets

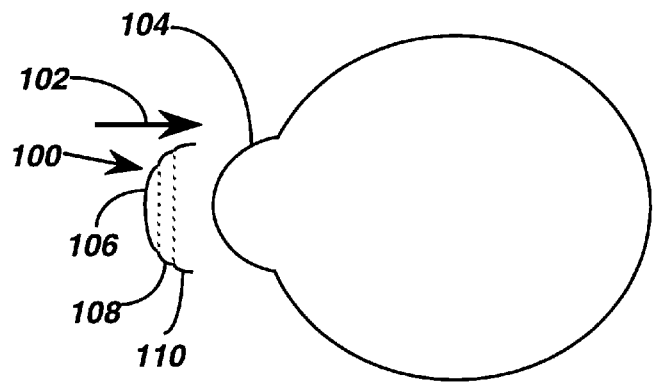
FIG. 1 *Prior Art*
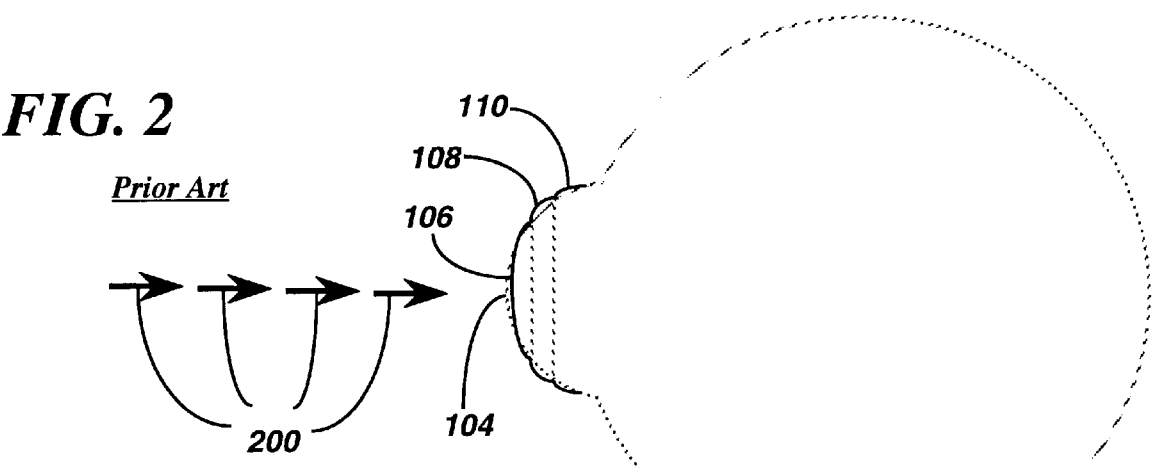
FIG. 2 *Prior Art*
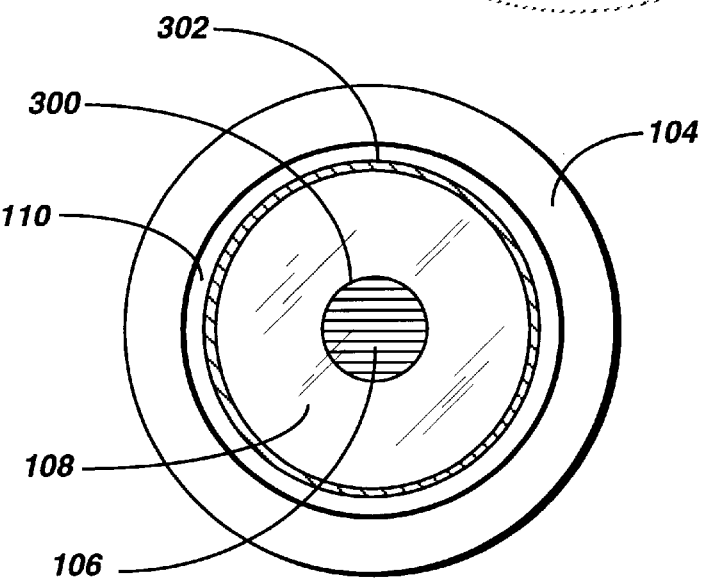
FIG. 3 *Prior Art*

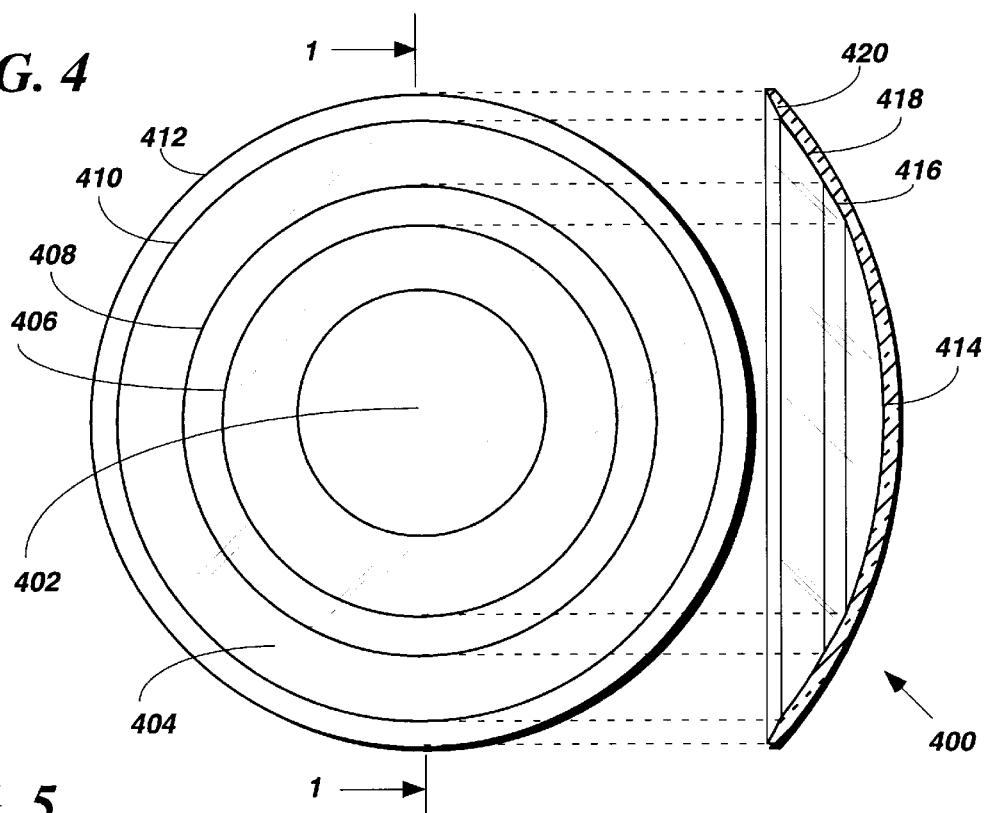
FIG. 4
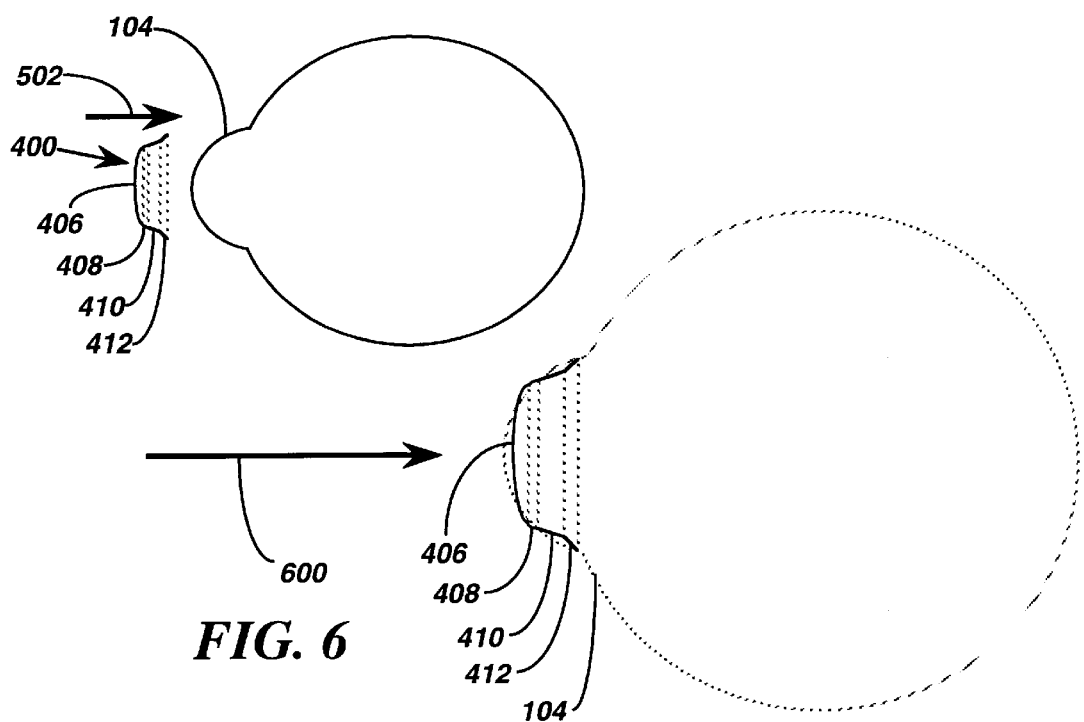
FIG. 5
FIG. 6

ORTHOKERATOLOGY CONTACT LENS AND METHOD THEREFOR

FIELD OF THE INVENTION

This invention relates generally to contact lenses, and more particularly, to a rigid gas permeable contact lens and a corresponding orthokeratology treatment method for improving visual acuity.

BACKGROUND OF THE INVENTION

A large portion of the population experience difficulty with their vision due to a number of possible conditions. The majority of vision problems in this portion result from a condition known as myopia, or nearsightedness. Myopia is a common condition where an eye cannot focus on far objects because the cornea of the eye is curved too steeply to provide adequate focusing at the retina of the eye. Alternatively, the eye may be afflicted with a condition know as hyperopia, or farsightedness. With hyperopia, the eye cannot focus on near objects because the cornea of the eye is curved too flatly to provide adequate focusing at the retina of the eye. Another common condition is astigmatism, where unequal curvature of one or more refractive surfaces of the cornea prevents light rays from focusing clearly at one point on the retina, resulting in blurred vision.

Conventional contact lenses with a longer central radius of curvature than the central radius of the cornea are known to change the shape of the cornea by compressing the surface at its apex. This "reshaped cornea" has a lengthened radius of curvature in its central zone, which serves to improve myopia, and to generally improve visual acuity. The procedure for obtaining this sort of correction to vision, where correction persists for some time after removal of the corrective lenses, is commonly known as orthokeratology.

Orthokeratology has been performed in some form or another since the early 1970's. Unfortunately, the time needed to achieve a desired visual correction using conventional orthokeratology can range from one to two years. Moreover, conventional orthokeratology is typically limited to correcting only 1.50 diopters of myopia, and the length of time in which this correction would "hold" before degrading is extremely variable, which regrettably necessitates wearing a retainer lens for at least part of the day.

Recent advances in orthokeratology have generated improvements in the amount of correction available. Present orthokeratology lenses can now typically correct up to 3.0 diopters of myopia. Furthermore, the time required to achieve correction has dropped from several years to several months on low to moderate myopes. However, the holding power associated with these improved orthokeratology treatments remains a problem. Even the best presently available orthokeratology treatment plan requires a patient to wear a retainer lens for some portion of their daytime or nighttime vision requirements, and in problem cases, possibly wear a retainer lens all the time to maintain corrected vision.

Thus, what is needed is a contact lens and corresponding orthokeratology treatment method that corrects substantial amounts of myopia, hyperopia, and astigmatism, over a short treatment period, and with substantial holding power that allows correction to last throughout a desired period of daytime and nighttime corrected vision.

BRIEF DESCRIPTION OF THE DRAWINGS

FIG. 1 is a side schematic outline view of a prior art orthokeratology contact lens in proximity to a cornea of a patient's eye.

FIG. 2 is a side schematic outline view illustrating the prior art orthokeratology contact lens and cornea of FIG. 1, the contact lens being shown fitted on the cornea.

FIG. 3 is front planar view of the prior art orthokeratology contact lens and cornea shown in FIG. 2.

FIG. 4 is a front planar view and a side sectional view of a contact lens in accordance with a preferred embodiment of the present invention.

FIG. 5 is a side schematic outline view of a contact lens in proximity to a cornea of a patient's eye, in accordance with the preferred embodiment of the present invention.

FIG. 6 is a side schematic outline view illustrating the contact lens and cornea of FIG. 5, the contact lens being shown fitted on the cornea according to the preferred embodiment of the present invention.

DESCRIPTION OF A PREFERRED EMBODIMENT

Referring to FIGS. 1, 2, and 3, the illustrations show, respectively, a side schematic outline view of a prior art orthokeratology contact lens in proximity to a cornea of a patient's eye, the contact lens of FIG. 1 being fitted on the cornea, and a front planar view of the prior art orthokeratology contact lens and cornea shown in FIG. 2, respectively.

The lens 100 illustrated in FIGS. 1, 2, and 3, is typical of present lenses used in conventional orthokeratology treatments. This contact lens 100 is typical of a reverse geometric contact lens that is commonly used today in conventional orthokeratology treatments. A typical reverse geometric contact lens has a base curve in the center, and a next curve that is steeper in curvature than the base curve, instead of flatter as in a conventional contact lens. Accordingly, the typical reverse geometric contact lens uses a longer radius of curvature at a central region 106 of the lens 100 to compress the central area of the cornea 104 when the lens 100 is fitted 102 on the cornea 104. The main advancement in orthokeratology provided by this contact lens 100 was that the radius of curvature of the region 108 of the contact lens surrounding the apex portion of the cornea 104 was steeper than the radius of the central region 106 of the contact lens 100 directly contacting and compressing a bearing area 300 on the apex portion of the cornea 104. As a consequence of the modified design, this contact lens 100 was able to center better than previous lenses on the anterior surface of the cornea 104 and thus elicit faster changes in the curvature of the central portion of the cornea 104. As mentioned before, the treatment times using this type of contact lens dropped from several years to several months.

According to the prior art orthokeratology treatment procedure associated with this reverse geometric contact lens 100, when the contact lens 100 started to show a significant bearing area 302 on the cornea 104 about the periphery region 110 of the contact lens 100, a change of contact lens 100 was recommended before an adverse physiological response occurred to a patient's eye. The periphery region 110 of the lens 100 was intentionally designed to only lightly touch the surface of the cornea 104 near the extreme outside edge of the lens 100. The only desired significant bearing area 300 on the cornea 104 was about the central portion of the cornea 104 resulting from the contact and compression by the central region 106 of the contact lens 100. This significant bearing area 300 on the central portion of the cornea 104 was understood to provide all the desired compression to the cornea 104 to improve a patient's myopia.

Initially, a lens 100 was fit 1 to 1.5 diopters flatter than the flattest "K" reading about the central portion of a patient's cornea. This lens 100 would "tighten up" very quickly on the cornea, making the lens 100 quickly unusable for continued correction of the patient's vision. Regrettably, this prior art orthokeratology treatment for improving a patient's myopia using the lens 100 required fitting the patient with up to three or more separate lenses per corrected eye over a period of up to several months of treatment. The rule was typically that one lens 100 was needed per diopter of desired correction. Accordingly, if a patient required correction of three diopters of myopia, at least three pairs of lenses 100 would be needed to correct the myopia, assuming the lenses 100 worked as predicted.

The lenses 100 are designed to provide progressively flatter curvature about the central region 106 of the lens 100 to maintain the required contact and compression about the central portion of the cornea 104 as the cornea 104 progressively forms to a desired shape that improves the patient's myopic condition. As the central portion of the cornea 104 recedes under the compression of the central region 106 of a first lens 100, the significant bearing area 300 on the central portion of the cornea 104 provides reduced compression force on the cornea 104, and an undesirable significant bearing area 302 develops about the periphery portion of the cornea 104. This condition reduces or eliminates the lens's ability to maintain itself centered about the central portion of the cornea 104. Essentially, the lens 100 "bottoms out" on the central portion of the cornea 104, providing minimal compression force to the central portion of the cornea 104 while exhibiting an extremely tight fit at the significant bearing area 302 on the periphery portion of the cornea 104.

As a patient's eyelid repeatedly blinks during the day, the eyelid blinks provide a repeated force 200 to the lens 100. This repeated force 200 from the eyelid blinking will normally provide compression to the lens 100 to transmit a normally desirable compression force to the central portion of the cornea 104. However, when the lens 100 "bottoms out" on the central portion of the cornea 104 the swiping of the eyelid across the lens 100 will also tend to provide an undesirable de-centering force to the lens 100, thus causing the lens 100 to move away from a centered position on the central portion of the cornea 104.

Previously, this was a basic problem with all orthokeratology treatments. When a lens 100 does not center correctly, the combination of the significant bearing area 302 about the periphery portion of the cornea 104 (off axis), a reduced bearing area 300 about the central portion of the cornea 104, and the de-centering of the lens 100 on the cornea 104 malform the cornea 104. The malformation is typically a round applanation (an abnormal flattening of a convex surface especially of the cornea or crystalline lens) area, and as the edge of this area starts to bisect the visual axis, "ghosting" occurs. This phenomena also decreases the holding power of the lens, increases the chance of abrasions, corneal ulcers, and various other problems.

Besides decreasing the holding power of the lens 100 on the cornea 104 thereby losing precision and effectiveness of treatment for myopia, misalignment of the lens 100 may also lead to abrasions of the cornea, corneal ulcers, and to various other problems of the eye. Accordingly, the above symptoms required immediately changing a first lens 100 to a second lens 100 that was designed and constructed to have a flatter curvature about the central region 106 of the lens 100 thereby allowing the central region 106 of the second lens 100 to again create a significant bearing area 300 on the central portion of the cornea 104 by contacting and compressing the central portion of the cornea 104, while again providing only a light touch area 302 about a periphery region 110 of the lens 100 on the periphery portion of the cornea 104.

This progressive lens replacement procedure could continue for a number of lenses over a number of months of orthokeratology treatment. According to the treatment procedure recommended for this lens 100, it is recommended to pre-design, manufacture, and have on-hand a series of progressively flatter lenses 100 for a patient, and to immediately fit a next lens 100 on the patient's eye when a significant bearing area 302 is detected about the periphery region 110 of the lens 100 on the periphery portion of the cornea 104. This progressive lens replacement procedure, therefore, tends to be a complicated and expensive treatment because of the continuous monitoring of the patient's eyes over several months of treatment. Moreover, because multiple lenses have to be pre-designed, pre-constructed, and are required to be on hand to immediately fit a patient's eye to progressively maintain contact and compression about the central portion of the cornea 104 of the patient, the direct and indirect costs associated with this procedure and lens 100 are high.

The region of the lens 100 between the central region 106 of the lens 100 and the peripheral region 110 of the lens 100 is called the tear reserve region 108 of the lens 100. The purpose of this tear reserve region 108 of the lens 100 is to allow tear fluid to collect in the tear reserve region 108 and to allow tear fluid to flow from the tear reserve region 108 to most of the anterior surface of the cornea 104. This tear fluid is understood to provide needed oxygen and lubrication to the anterior surface of the cornea 104. The tear reserve region 108 additionally assures that tear fluid would be available under the lens 100 to oxygenate and lubricate the surface of the cornea 104 underlying the lens 100 when external tear flow to the cornea 104 would be sealed off. Tear flow to the cornea 104 under the lens 100 can be sealed off by the significant bearing area 302 being created about the periphery portion of the cornea 104 when the lens 100 approaches a "bottom out" condition on the cornea 104. Unfortunately, in a tear seal-off condition, the tear fluid provided from the tear reserve region 108 may not provide sufficient oxygen to the cornea 104 for an extended period of time, possibly resulting in hypoxia and other damage to the cornea 104. This tear seal-off condition, therefore, increased the medical urgency to immediately replace a lens 100 upon detection of a "bottom out" condition of the lens 100 on the cornea 104, i.e., when a significant bearing area 302 was detected about the periphery portion of the cornea 104.

Lastly, although this contact lens 100 was able to reduce the time required to obtain a final result for improving myopia down to approximately one to three months on low to moderate myopes, thereafter a retainer contact lens was still required to be used by the patient for part, or most, of the day to maintain a desired visual acuity during their daytime or nighttime vision requirements.

Referring to FIG. 4, the illustration shows a front planar view and a side sectional view of a contact lens 400 in accordance with a preferred embodiment of the present invention.

The exemplary lens 400 illustrated in FIG. 4 preferably has four correction zones. As a comparison, the prior art lens 100 typically was designed with three major correction zones. The four correction zones of the present invention, listed from the center of the lens to the outer periphery of the lens, are: a) an optical zone 406, a fitting zone 408, an alignment zone 410, and a peripheral zone 410.

The first zone is the optical zone 406, having a curvature defined by a base curve 414. The optical zone 406 applies a primary compressive force to a region substantially centered at an apical center of the cornea 104, and is responsible for the corrective flattening or decrease in the radius of curvature of the central cornea during treatment. Since the radius of curvature of the base curve 414 is greater than a measured curvature of a central portion of the cornea 104, the optical zone 406 contacts the central portion of the cornea 104 and creates a central bearing area 402 where a primary compressive force is applied during vision correction. An alternative way of stating the shape of the base curve 414 is that its curvature is less than (flatter than) a measured curvature of the central portion of the cornea 104. Specifically, as the radius of curvature of a curve increases, the curve's curvature as measured over a fixed segment of its arc flattens. Typically, the optical zone 406 is 6 millimeters (mm) in diameter, but can be larger or smaller depending on the shape of the cornea and the amount of central corneal radius decrease desired to achieve correction. Moreover, the radius associated with the base curve 414 can trace a spherical, aspherical or arbitrary curved path if necessary, to effect visual correction.

The second zone is a fitting zone 408. This zone has a radius of curvature defined by a predefined fitting curve 416 (first peripheral curve), said radius of curvature being less than (shorter) the radius of curvature associated with the base curve 414. This shorter radius of curvature of the fitting zone 408 yields a curvature substantially steeper than each of the measured curvature of the central portion of the cornea and the measured curvature of the portion of the cornea circumscribing the central portion of the cornea. Accordingly, the fitting zone 408 acts as a transition region between the optical zone 406 and an alignment zone 410 by linking an edge of the optical zone 406 to an edge of the alignment zone 410. Essentially, the fitting zone 408 is designed to bring the posterior surface of the contact lens (from the optical zone 406) to a bearing relationship on the central portion of the cornea 104 and to provide compression force to the optical zone (base curve portion of the lens) 400 and thereby to the central portion of the cornea 104 while correcting the patient's visual acuity. The fitting zone 408 may be composed of any alternative combination of shapes of curves that effect the above design purpose. Additionally, the degree of bearing created on the central portion of the cornea 104 by the fitting zone 408 can be modified to either tighten or loosen the fit of the contact lens 400. The curvature of the fitting curve can be pre-defined to increase or decrease the amount of compression force to deliver to the central portion of the cornea while correcting visual acuity. Nominally, the curvature of the fitting curve is selected to maintain contact and compression on the central portion of the cornea 104 during a selected or desired diopter correction of the central portion of the cornea 104. The fitting zone 408 is typically 0.6 mm in width, but can be wider or narrower depending on the specific shape and bearing relationships needed to achieve the desired visual correction.

The third zone is an alignment zone 410. The alignment zone 410 is designed to provide and maintain centration of the lens 400 by having a radius of curvature either the same or shorter than the cornea 104. A predefined alignment curve 418 defines the curvature of the alignment zone 410, which in the preferred embodiment is less than the measured curvature of the portion of the cornea circumscribing the central portion of the cornea. The alignment zone 410 creates a large bearing area 404 in a region corresponding with the portion of the cornea 104 circumscribing the central portion of the cornea 104 where a centering force is created that maintains the optical zone substantially at the apical center of the cornea 104. The alignment zone 410 further produces a secondary compressive force in the large bearing area that cooperates with the primary compressive force to flatten the central portion of the cornea during vision correction.

Alternatively, the alignment zone 410 can be segmented into multiple curves and any combination of any shapes of curves, so long as sufficient bearing area is maintained to create and maintain the centering force and secondary compressive force while correcting visual acuity. The width of the alignment zone 410 is typically 1 mm, but can be wider or narrower depending on the fitting characteristics desired and the particular shape factors of the cornea 104.

The fourth zone is the peripheral zone 412. The peripheral zone 412 is designed with a radius of curvature longer that the cornea, yielding a curvature slightly less than a measured curvature of a portion of the cornea circumscribing an area beyond an outside edge of the portion of the cornea circumscribing the central portion of the cornea that corresponds to the alignment zone 410. More simply, the peripheral zone 412 has its surface contour defined by a predefined peripheral curve 420 which has a curvature that nearly parallels the portion of the cornea underneath it. The peripheral zone 412 promotes tear flow under the contact lens by taking advantage of a tear pumping action created when the individual blinks the eyelid. Additionally, the peripheral zone 412 is designed to create a slight edge lift which allows easy contact lens removal from the cornea.

The different radii used to define the base curve 414, fitting curve 416, alignment curve 418, and peripheral curve 420 in this new lens design 400 are calculated after careful examination of the eye and the associated ocular tissue. The corneal curvature must be measured, the proper contact lens power defined and the anticipated physiological response to the contact lens must be determined. An individual skilled in the examination techniques of the ocular system is typically capable of performing these tasks.

The lens design shown in FIGS. 4, 5, and 6, cuts against the conventional wisdom in orthokeratology lens design by implementing and using to its advantage the very thing that all the other prior art lens 100 designs were made to avoid, a significant bearing area 404 about a periphery of the lens 400. This significant bearing area 404, which is advantageously utilized in the instant inventive lens 400, was desperately avoided in prior art lens 100 systems to try to avoid a peripheral tear seal-off condition under the prior art lens 100. Peripheral seal-off occurs when the contact lens 400 touches the cornea 104 to such an extent that tear flow is compromised or cut-off. The complications previously experienced by orthokeratology patients wearing conventional orthokeratology lenses 100 that caused peripheral seal-off are related to the fact that the cornea 104 needs oxygen to carry on its metabolism. However, in the present invention, this oxygen is advantageously delivered by the tear pumping action of the contact lens 400 supplying fresh oxygenated tears to all parts of the cornea under the lens 400 by oxygen perfusion through the contact lens-tear layer interface. When peripheral seal-off occurred using prior art lenses 100, no new tears could get to the cornea. This was because the prior art contact lens-tear layer barrier typically did not allow the cornea enough oxygen to carry on it's metabolism. Thus, the cornea's metabolism switched from aerobic to anaerobic metabolism with the resultant metabolic byproducts and corneal hypoxia. This condition causes corneal breakdown and must be strictly avoided. With the new lens 400 design, this problem is completely avoided because the peripheral curve portion 412 of the lens 400 operates to pump tear fluid across the perceived barrier, thus providing lubrication and oxygen to the anterior surface of the cornea 104 under the lens 400. Moreover, the new lens design 400 makes strategic use of the physical forces present in general contact lens wear such as the force due to a blinking eyelid, eyeball movement, and hydraulic fluid forces of the tears. By appropriately directing these forces through the use of a plurality of specifically curved correction regions, the new lens design 400 is able to solve problems seen in the prior art such as centration, corneal wetting, and corneal respiration, and do so with a single lens 400 rather than a series of lenses as required by prior art lens designs. Essentially, this invention allows a doctor to design the first lens 400 as the only lens needed to achieve visual correction.

The preferred contact lens 400 is manufactured of material consisting of a gas permeable plastic that allows greater amounts of oxygen to penetrate the matrix of the lens 400. In the present invention, the tear layer is reduced in thickness by the new contact lens 400 while the contact lens-tear layer interface allows sufficient oxygen to the cornea to prevent corneal hypoxia. Additionally, alternative structures can be fabricated using hybrid lens systems, e.g., a combination of hard, semi-hard, and soft lens materials, that will achieve comparably successful results in correcting visual acuity.

Another advantage of the new lens design is that it specifically inhibits the undesired sphericallization of the cornea, which was mistakenly thought to be a treatment goal in prior art orthokeratology designs. The fitting zone 408 serves to condense the displaced corneal mass and repositions it to conform with more of the posterior surface of the optical zone 406 in conformity with the base curve 414 during correction of visual acuity. This results in a larger area about the central portion of the cornea 104 that is of the desired radius of curvature according to the base curve 414, and significantly longer retention of the desired corneal shape for corrected vision after the lens 400 has been removed. It is not uncommon for an eye treated with this lens to retain the desired visual correction for 12 to 18 hours after lens removal, without the use of a retainer lens. No prior art lens even comes close to this claim, as most prior art lenses have holding power durations of less than eight hours. Moreover, due to the cooperative dual-zone compression scheme created by the optical zone and the alignment zone, this lens 400 re-shapes the cornea significantly faster than a prior art retainer lens 100, thus requiring the shortest period of lens wear to maintain corrected vision. The preferred lens 100, according to the present invention, serves as both the primary correction lens and as a retainer lens to maintain correction once achieved. For example, a patient may wear the lens as a retainer lens during a sleep period, such as during the night. This procedure, known as night therapy, allows the individual to remove the lenses 400 during a waking period and experience corrected vision without wearing a retainer lens 400 until the following sleep period, e.g., until the next night. Therefore, during waking periods, the individual may benefit from corrected vision without having to wear the lens 400 as a retainer lens. This is a significant improvement over any known prior art orthokeratology lenses 100.

As discussed earlier, conventional wisdom taught that only a very light touch area in the peripheral curve portion of prior orthokeratology art lenses 100 was acceptable. Further, any detection by a doctor of a significant bearing area about the periphery of the prior art lens 100 required immediate replacement of the lens 100. In direct contrast, the new lens 400 has a large bearing area 404 in the peripheral zone 412. Conventional wisdom limited prior art designs to using this light touch area based on a fear that use of a large bearing area 302 would create a poor physiological response of the cornea caused by a lens "bottom out" condition or a tear seal-off condition, typically resulting in hypoxia, stippling, tissue breakdown, anaerobic respiration, tear stagnation, abrasions, ulcers, etc. Additionally, prior art designs came down sharply in the transition area, that area between the traditional base curve at the center of the lens and the peripheral curve, while the new lens 100 transitions gradually into more of an alignment fit, i.e., a fit that more nearly matches the radius of curvature of the cornea 104 in the region of the alignment curve 410.

With the new contact lens 400, you have the first bearing area due to the pressure placed on the apex of the eye by the optical zone 406 and corresponding base curve 414, and the second bearing area is due to pressure placed on the eye by the alignment zone 410 and corresponding alignment curve 418. This dual compression mechanism potentates the effect of reshaping the cornea to achieve the desired visual correction. The corneal tissue actually squeezes up into the areas where the alignment zone 410 and fitting zone 408 are located. Since the prior art taught that no significant compression force should be exerted on the cornea about the area occupied by the present invention's alignment zone 410, the dual compression effect achieved with the instant invention, that potentates the corneal shaping effect by using dual compression zones on the cornea 104 could not be achieved with the prior art lenses 100. The preceding contention is clearly supported in prior art lens fitting instructions and nomograms, which show a bright ring of fluorescein around the periphery of the lens, indicating a fit that was considered too tight, and according to the prior art, wearing a lens that fit like this would not only cause adverse physiological effects, but it would not correct the patient's vision.

The net results are that the new lens 400 design elicits faster and more stable corneal changes thereby reducing chair time, e.g., the time a doctor must commit per patient for "in office" treatments, requires fewer contact lens changes since the first pair of lenses are designed and intended to be the only pair of lenses, and thus reduces the overall costs, complexity, and length, of the orthokeratology treatment. No other known lens design utilizes specifically calculated radii to achieve the bearing relationships described herein according to the preferred embodiment present invention, or achieve the advantages seen with the new lens design.

Referring to FIG. 5, the illustration shows the contact lens 400 before being placed 502 on the cornea 104.

The optical zone 406, also known as the base curve portion 406 of the lens 400, has a curvature initially selected to have a diameter of 6.0 mm. If it's selected too small, say 5.0 mm, if a lens de-centers on a nominal size cornea 104, ghosting may occur as the optical zone 406 moves away from the corneal apex, and the un-centered bearing area may cause unwanted deformation in the central optical zone of the cornea 104. Although optical zones 406 with diameters as small as 3 mm, or with diameters greater than 8 mm, are possible, the preferred diameter is approximately 6 mm.

A small (<6 mm) optical zone 406 results in decreased bearing area on the central portion of the cornea 104 due to the contact lens 400. This requires a shallower fitting curve 416 which pushes the alignment curve 418 closer in, ultimately increasing the dual compression area. Conversely, a large (<6 mm) optical zone 406 results in increased bearing area on the central cornea 104 due to the contact lens 400. This requires a steeper fitting curve 416 which pushes the alignment curve 418 further out, and ultimately reduces the dual compression area.

The next zone is the fitting zone 408, also known as the fitting curve portion 408 of the lens 400, or which is initially 0.6 mm wide. Although the fitting zone 408 may be constructed with current manufacturing technology to a width as small as approximately 0.4 mm, with improving manufacturing techniques and equipment the fitting zone 408 may be constructed to have a much smaller width as needed. The radius of curvature in this curve 416 can be 6–14 diopters steeper than the base curve 414. By comparison, the new lens 400 is 3–5 times steeper in curvature in this area than prior art lenses 100. The degree of steepness in this area is defined in relation to the curvature of the cornea 104. To reiterate, the fitting curve 416 is designed to bring the posterior surface of the lens 400 into the correct positioning to contact and provide compression force to the central portion of the cornea 104 while correcting visual acuity. The correct positioning is determined by the actual amount of change in the shape of the central portion of the cornea 104 that is desired to correct vision, and the fitting characteristics of the lens 400. The actual determination of where the corneal surface lies is presently estimated with a keratometer. Other methods which are available are the topographers, or any other instrument that can determine the spatial positioning or mapping of the corneal surface. Presently, the best results have been achieved using the keratometer.

The next zone is the alignment zone 410, also known as the alignment curve 418 portion of the lens 400. This alignment zone 410 initially has substantially the same radius of curvature as the central corneal curve as measured by the keratometer. What that effectively does is make the lens slightly steeper (or tighter) than the actual cornea surface under that area of contact about the alignment zone 410, resulting in some compression in the area. The associated alignment curve 418 creates a bearing zone over a large surface area of the cornea 104, which causes the lens to maintain good alignment of the lens with respect to the apex of the cornea. Typical width of the alignment zone 410 is 1.0 mm, but this may vary. As stated before, the prior art teaches that placement of a correction zone in the region where the alignment zone 410 is located will create an adverse physiological response, e.g., creating undesirable effects such as tear seal-off, which may lead to corneal hypoxia and tissue damage due to anaerobic respiration or the like. However, in conjunction with the design of the fitting zone 408, its transition region to the alignment zone 410, and the peripheral zone 412, the alignment zone 410 in the present invention allows the lens to move and automatically self-align while promoting tear flow across the wide bearing area, thus avoiding any of the problems associated with the prior art reverse geometry orthokeratology lenses 100.

The final or peripheral zone 412, also known as the peripheral curve 420 portion of the lens 400, has a typical width of 0.4 mm. This is determined based on the desired overall diameter of the lens 400, which is typically 10.0 mm. Presently, the peripheral curve 420 is typically pre-defined to approximately 10.5 mm in radius, but this may be modified on an individual basis to allow for more tear flow across the zone. This curvature is chosen slightly flatter than the cornea, allowing fairly good lens movement without being too tight, and creating a slight amount of lift to the lens 400 so the lens 400 can be easily removed. Because the curvature is slightly flatter than the cornea 104, fluorescein can be seen under the edge of the lens 400 when examined, representing tear fluid flowing across the peripheral zone 412 and to the rest of the interface between the lens 400 and the cornea 104. This tear flow allows constant lubrication and oxygenation of the lens-cornea interface and results in a more comfortable and wearable lens 400.

Referring to FIG. 6, the illustration shows the contact lens 400 placed on the cornea 104. Note that when fit 502 to the cornea 104, the tear layer thickness would be negative at the corneal apex. That is, the center of the lens 400 is designed using a curve that is flatter than the curvature of the eye about the central portion of the cornea 104. This results in a central area of the lens 400 that will tend to flatten (decrease the curvature of) the center of the cornea 104. However, since the cornea is a compliant structure, the compression force 600 applied by the eyelid in the central optical zone 406 is transmitted to the central portion of the cornea 104 and serves to reshape the central portion of the cornea 104 by decreasing the overall radius of curvature of the cornea 104 about the central optical zone 406 as well as about an area surrounding and proximate to the central optical zone 406.

Further, as was discussed above, a patient using a lens 400 according to the instant invention is able to advantageously wear the lens 400 during a continuous sleep period to help shorten their vision correction period. Specifically, the resting eyelid provides a relatively continuous compression force 600 to the lens 400 thereby helping to significantly shorten the vision correction period over any known orthokeratology lens 100 and method. As discussed above, known vision correction methods and lenses 100 typically required patients to wear the prior art lenses 100 during a waking, e.g., daytime, period. Accordingly, the patient wearing the prior art lenses 100 helped to shorten their vision correction period only by providing short bursts of compression force 200 (see FIG. 2) provided from short blinking cycles of the patient's eyelid while wearing the prior art lenses 100 during a waking period, e.g., during the day. This, again, is a significant advantage of the present lens 400 over any known prior art lens 100 and method.

Referring again to FIG. 6, as the distance from the apex of the cornea 104 and the center of the lens 400 increases, the distance between the radius of curvature of the cornea 104 and the posterior surface of the lens 400 typically also increases, as shown by a thickening of the tear layer, up to the end of the optical zone 406. Another way of describing the relationship between the surface of the cornea and the posterior surface of the lens 400 is that as the lens 400 is fit flatter on the cornea, the distance between the surface of the cornea and the posterior surface of the lens increases about the outer periphery of the optical zone 406 and into the fitting zone 408, as represented by a thickening tear layer. Referring now to the fitting curve portion 408 of the lens 400, it is designed to maintain the posterior surface of the lens 400 about the central portion of the cornea 104 to the anterior surface of the cornea 104 during visual correction. If the cornea 104 were a perfect sphere, perfect alignment would be achieved at the point of zero tear layer thickness transition. However, as stated before, the cornea is not a perfect sphere, and should not be formed by a lens as such since this does not yield optimal visual correction.

One of ordinary skill in the art of orthokeratology will appreciate that the physical embodiments and procedures discussed herein represent only several ways in which the new technology can be applied to achieve vision correction. Accordingly, one can expect that the specific correction zones and their associated shapes may be adjusted to specifically conform to each patient's vision correction requirements, without deviating from the teachings of the present invention.

What is claimed is:

1. A contact lens, comprising:
    an optical zone having a curvature less than a measured curvature of a central portion of a cornea, the optical zone creating a central bearing area in a region substantially centered at an apical center of the cornea where a primary compressive force is applied during vision correction; and
    an alignment zone coupled to the optical zone and having a curvature greater than a measured curvature of a portion of the cornea circumscribing the central portion of the cornea, the alignment zone creating a large bearing area in a region corresponding with the portion of the cornea circumscribing the central portion of the cornea where a centering force is created that maintains the optical zone substantially at the apical center of the cornea, the alignment zone further producing a secondary compressive force in the large bearing area that cooperates with the primary compressive force to flatten the central portion of the cornea during vision correction.

2. The contact lens according to claim 1, wherein the contact lens is constructed from a gas permeable material.

3. The contact lens according to claim 1, wherein a predefined base curve defines the curvature of the optical zone of the contact lens.

4. The contact lens according to claim 1, wherein a predefined alignment curve defines the curvature of the alignment zone of the contact lens.

5. The contact lens according to claim 1, comprising:
    a fitting zone having a curvature substantially greater than each of the measured curvature of the central portion of the cornea and the measured curvature of the portion of the cornea circumscribing the central portion of the cornea, the fitting zone acting as a transition region between the optical zone and the alignment zone such that an edge of the optical zone is linked via the fitting zone to an edge of the alignment zone.

6. The contact lens according to claim 5, wherein the contact lens is constructed from a gas permeable material.

7. The contact lens according to claim 5, wherein a predefined fitting curve defines the curvature of the fitting zone.

8. The contact lens according to claim 1, comprising:
    a peripheral zone having a curvature slightly less than a measured curvature of a portion of the cornea circumscribing an area beyond an outside edge of the portion of the cornea circumscribing the central portion of the cornea that corresponds to the alignment zone, the peripheral zone acting to promote tear flow under the contact lens and to allow easy contact lens removal from the cornea.

9. The contact lens according to claim 8, wherein the contact lens is constructed from a gas permeable material.

10. The contact lens according to claim 8, wherein a predefined peripheral curve defines the curvature of the peripheral zone.

11. A contact lens, comprising:
    a base curve portion of the lens, having a longer radius of curvature than a central portion of a cornea of a patient, for contacting and providing compression force to the central portion of the cornea when the contact lens is fitted to the patient's eye;
    a first peripheral curve portion of the lens circumscribing and coupled to, and having a substantially shorter radius of curvature than, the base curve portion of the lens for providing compression force to the base curve portion of the lens, and for maintaining contact and providing compression force from the base curve portion of the lens to the central portion of the cornea while correcting the patient's visual acuity; and
    a second peripheral curve portion of the lens, circumscribing and coupled to the first peripheral curve portion of the lens, and having a shorter radius of curvature than an underlying peripheral portion of the cornea for contacting the underlying peripheral portion of the cornea and for substantially providing compression force thereto, the compression force of the second peripheral curve portion of the lens cooperatively operating in combination with the compression force of the base curve portion of the lens for molding the cornea to induce a longer radius of curvature at the central portion of the cornea and for correcting the patient's visual acuity.

12. A reverse geometry orthokeratology lens, comprising:
    a base curve portion of the lens, having a flatter curvature than a central portion of a cornea of a patient, for contacting and providing compression force to the central portion of the cornea when the lens is fitted to the patient's eye;
    a fitting curve portion of the lens circumscribing and coupled to, and having a substantially steeper curvature than, the base curve portion of the lens for providing compression force to the base curve portion of the lens, and for maintaining contact and providing compression force from the base curve portion of the lens to the central portion of the cornea while correcting the patient's visual acuity; and
    an alignment curve portion of the lens, circumscribing and coupled to the fitting curve portion of the lens, and having a steeper curvature than an underlying peripheral portion of the cornea for contacting the underlying peripheral portion of the cornea and for providing compression force thereto, the compression force of the alignment curve portion of the lens cooperatively operating in combination with the compression force of the base curve portion of the lens for molding the cornea to induce a flatter curvature at the central portion of the cornea and for maintaining alignment of the lens on the cornea while correcting the patient's visual acuity.

13. A reverse geometry orthokeratology lens for correcting myopia in a patient's eye, comprising:
    a base curve portion of the lens, having a flatter curvature than a central portion of a cornea of a patient, for contacting and providing compression force to the central portion of the cornea when the lens is fitted to the patient's eye;
    a fitting curve portion of the lens outwardly peripherally connected to, and having a substantially steeper curvature than, the base curve portion of the lens for providing compression force to the base curve portion of the lens, and for maintaining contact and providing compression force from the base curve portion of the lens to the central portion of the cornea while correcting the patient's myopia;
    an alignment curve portion of the lens, outwardly peripherally connected to the fitting curve portion of the lens, and having a wide annular surface that has a steeper curvature than an underlying peripheral portion of the cornea for contacting the underlying peripheral portion of the cornea and for providing compression force thereto, the compression force of the alignment curve portion of the lens cooperatively operating in combination with the compression force of the base curve portion of the lens for molding the cornea to induce a flatter curvature at the central portion of the cornea and for maintaining alignment of the lens on the cornea while correcting the patient's myopia; and a peripheral curve portion of the lens, outwardly peripherally connected to the alignment curve portion of the lens, and having a flatter curvature than an underlying peripheral portion of the cornea for allowing tear flow across the peripheral curve portion of the lens for providing tear flow between the lens and the cornea to lubricate and oxygenate the cornea while wearing the lens for correcting the patient's myopia.

14. A method for fitting a contact lens to a cornea of a patient's eye, the contact lens comprising a base curve portion of the lens for contacting a central portion of the cornea and a peripheral curve portion of the lens circumscribing the base curve portion of the lens for contacting a peripheral portion of the cornea, the base curve portion of the lens having a longer radius of curvature than the central portion of the cornea and the peripheral curve portion of the lens having a wide annular surface that has a shorter radius of curvature than the peripheral portion of the cornea, the method comprising the steps of:

(a) contacting and compressing the central portion of the cornea about the apex of the cornea with the base curve portion of the lens while correcting the patient's visual acuity with the contact lens; and (b) contacting and compressing the peripheral portion of the cornea with the peripheral curve portion of the lens while correcting the patient's visual acuity with the contact lens, the compressing by the peripheral curve portion of the lens cooperatively operating in combination with the compressing by the base curve portion of the lens thereby molding the cornea to induce a longer radius of curvature at the central portion of the cornea while correcting the patient's visual acuity with the contact lens.

15. The method of claim 14, further comprising the step of:

(c) providing tear flow to the peripheral portion of the cornea and the central portion of the cornea by allowing tear flow between the lens and the cornea while substantially contemporaneously performing steps (a) and (b).

* * * * *